United States Patent
He et al.

(10) Patent No.: US 7,674,945 B2
(45) Date of Patent: Mar. 9, 2010

(54) PROCESS FOR ALKYLATION OF AN AROMATIC HYDROCARBON OR ISOALKANE WITH AN OLEFIN OVER THE CATALYSIS OF A SOLID ACID

(75) Inventors: Yigong He, Beijing (CN); Zheng Man, Beijing (CN)

(73) Assignee: China Petroleum & Chemical Corporation, Beijing (CN)

( * ) Notice: Subject to any disclaimer, the term of this patent is extended or adjusted under 35 U.S.C. 154(b) by 786 days.

(21) Appl. No.: 10/586,510

(22) PCT Filed: Jan. 19, 2005

(86) PCT No.: PCT/CN2005/000087

§ 371 (c)(1),
(2), (4) Date: Jul. 18, 2006

(87) PCT Pub. No.: WO2005/070854

PCT Pub. Date: Aug. 4, 2005

(65) Prior Publication Data

US 2007/0118005 A1    May 24, 2007

(30) Foreign Application Priority Data

Jan. 19, 2004    (CN) .................... 2004 1 0000958

(51) Int. Cl.
*C07C 2/60* (2006.01)
*C07C 2/68* (2006.01)

(52) U.S. Cl. .............. 585/731; 585/906; 585/462; 585/463; 585/465; 585/466; 585/726; 585/727; 585/729

(58) Field of Classification Search .......... 585/906, 585/462, 463, 465, 466, 726, 727, 729, 731
See application file for complete search history.

(56) References Cited

U.S. PATENT DOCUMENTS

| | | | |
|---|---|---|---|
| 3,231,517 A * | 1/1966 | Bloch et al. ........... | 502/230 |
| 3,549,557 A | 12/1970 | Bolton et al. | |
| 3,644,565 A | 2/1972 | Biale | |
| 3,647,916 A | 3/1972 | Ceaser et al. | |
| 3,917,738 A | 11/1975 | Fenske et al. | |
| 3,962,133 A | 6/1976 | Rodewald | |
| 4,116,880 A | 9/1978 | Olah | |
| 4,384,161 A | 5/1983 | Huang | |
| 5,012,033 A | 4/1991 | Child et al. | |
| 5,120,897 A | 6/1992 | Del Rossi et al. | |
| 5,157,196 A | 10/1992 | Crossland et al. | |
| 5,157,197 A | 10/1992 | Cooper et al. | |
| 5,190,904 A | 3/1993 | Crossland et al. | |
| 5,220,095 A | 6/1993 | Hommeltoft et al. | |
| 5,221,777 A | 6/1993 | Huss, Jr. et al. | |
| 5,245,101 A | 9/1993 | Del Rossi et al. | |
| 5,288,685 A | 2/1994 | Kallenbach et al. | |
| 5,324,881 A | 6/1994 | Kresge et al. | |
| 5,346,676 A | 9/1994 | Crossland et al. | |
| 5,364,976 A | 11/1994 | Kallenbach | |
| 5,391,527 A | 2/1995 | Kojima et al. | |
| 5,475,178 A | 12/1995 | Del Rossi et al. | |
| 5,489,729 A | 2/1996 | Benazzi et al. | |
| 5,731,256 A | 3/1998 | Benazzi et al. | |
| 5,739,074 A | 4/1998 | Kocal et al. | |
| 6,103,947 A | 8/2000 | Barger | |

FOREIGN PATENT DOCUMENTS

| | | |
|---|---|---|
| CN | 1062307 | 7/1992 |
| CN | 1125639 | 7/1996 |
| CN | 1125640 | 7/1996 |
| CN | 1184797 | 6/1998 |
| CN | 1232814 | 10/1999 |
| CN | 1246467 | 3/2000 |
| CN | 1331065 | 1/2002 |
| CN | 1340491 | 3/2002 |
| EP | 714 871 | 6/1996 |
| GB | 1389237 | 4/1975 |
| GB | 1432720 | 4/1976 |
| JP | 1245853 | 10/1989 |
| WO | WO 94/03415 | 2/1994 |
| WO | WO 95/26815 | 10/1995 |
| WO | WO 2005/070854 | 8/2005 |

OTHER PUBLICATIONS

International Search Report from PCT/CN2005/000087 dated May 19, 2005.
Hutson, Jr, Thomas et al "Phillips HF Alkylation Process for Alkylation of C3 C4 and C5 Olefins" pp. I-23-I-28, Chapater 1.2 Handbook of Petroleum Refining Processes, 1996.
Albright, LF et al "Alkylation of Isobutane with C4 Olefins. 1. First-Step Reactions Using Sulfuric Acid Catalyst", Ind Eng Chem Res 1988, 27, 381-386.
Albright, LF et al "Alkylation of Isobutane with C4 Olefins. 2. Production and Characterization of Conuunct Polymers", Ind Eng Chem Res 1988, 27, 386-391.
Albright, LF et al "Alkylation of Isobutane with C4 Olefins. 3. Two-Step Process Using Sulfuric Acid as Catalyst", Ind Eng Chem Res 1988, 27, 291-397.
Oil Refining Technology in China, China Petrochemical Press, pp. 206-217, 1991.
Written Opinion from PCT/CN2005/00087 dated May 19, 2005.
International Preliminary Report on Patentability from PCT/CN2005/00087 dated Dec. 21, 2005.

* cited by examiner

*Primary Examiner*—Thuan Dinh Dang
(74) *Attorney, Agent, or Firm*—Calfee, Halter & Griswold LLP

(57) ABSTRACT

The present invention discloses a process for alkylation of an aromatic hydrocarbon or isoalkane with an olefin over the catalysis of a solid acid, comprising contacting a reaction material containing an aromatic hydrocarbon or $C_4$-$C_6$ isoalkane, $C_2$-$C_{18}$ monoolefin and a compound containing a strongly electronegative element as promoter with a solid acid catalyst to carry out the alkylation, characterized in that the solid acid catalyst is contacted with a compound having a strongly electronegative element prior to its contact with the reaction material. Said process not only greatly increases the selectivity of the target product of the alkylation but also improves stability of the solid acid catalyst.

12 Claims, No Drawings

PROCESS FOR ALKYLATION OF AN AROMATIC HYDROCARBON OR ISOALKANE WITH AN OLEFIN OVER THE CATALYSIS OF A SOLID ACID

CROSS REFERENCE TO RELATED APPLICATIONS

The present application is the U.S. national phase entry of PCT/CN2005/000087 with an international filing date of Jan. 19, 2005 and claims priority from CN Patent Application Serial No. 200410000958.7, filed Jan. 19, 2004, which are both incorporated by reference in their entirety.

TECHNICAL FIELD

The present invention relates to a process for alkylation, and more particularly to a process for alkylation of an aromatic hydrocarbon or isoalkane with an olefin over the catalysis of a solid acid.

BACKGROUND ART

At present, there are a lot of hydrocarbon conversion processes using solid acid catalysts at low temperatures, such as alkylation (alkylation of an isoalkane with an olefin, and alkylation of benzene with an olefin), isomerization (isomerization of $C_4$, $C_5$ and $C_6$ low-carbon n-alkanes, and isomerization of low-carbon olefins), olefin oligomerization, hydroisomerization and the like. These low temperature hydrocarbon conversion processes require solid acid catalysts having strong acidity, such as supported heteropoly acid catalysts, supported heteropoly acid salt catalysts, zeolite-molecular, sieve catalysts, $SO_4^{2-}$/oxide super acid catalysts, supported Brönsted-Lewis conjugated solid super acid catalysts, solid polymerization ion exchange resins and oxide or molecular sieve catalysts treated with Brönsted acids or Lewis acids. These solid acid catalysts participate in hydrocarbon conversion reactions according to the reaction mechanism of carbenium ions.

The above-mentioned alkylation of an isoalkane with an olefin refer to the reactions of $C_4$-$C_6$ isoalkanes with $C_3$-$C_6$ monoolefins to produce isomerized long-chain alkanes. An example of the products of the alkylation is $C_8$ isooctane produced in the reaction of isobutane with butene, which has a high octane number and a low Reid vapor pressure, and is useful as an excellent additional component for gasoline.

Here, the industrially used catalyst of the above-mentioned alkylation processes is $H_2SO_4$ or HF, which has a concentration of about 95%. $H_2SO_4$ alkylation processes carried out at a low temperature (about 10° C.) can prevent olefins from building-up reactions, but they will produce a big amount of waste acids, which cannot be recycled and will pollute the environment seriously if discharged. HF alkylation processes are carried out at a low temperature (generally between 20 and 40° C.), too, but HF is easily volatile and can easily cause environmental pollution and harm the production environment. The industrial use of $H_2SO_4$ and HF for the production of alkylate oils has lasted for several decades, and "Alkylation of isobutane with $C_4$ olefins", Ind. Eng. Chem. Res., 27, 381-379 (1988), *Handbook of Petroleum Refining Processes*, 1, 23-28 (1986) and *Oil Refining Technology in China*, China Petrochemical Press, 206-217 (1991) contain detailed discussions about it.

Since $H_2SO_4$ and HF as strong liquid acids pollute the environment seriously, it has become an important research subject for the researchers in the international catalyst field to use solid acids to replace them as alkylation catalysts. Recently, various solid acid catalysts used in the above-mentioned alkylation processes are reported, such as the $SO_4^{2-}$/oxide super acidic catalysts disclosed in JP01,245,853, U.S. Pat. No. 3,962,133, U.S. Pat. No. 4,116,880, GB1,432,720 and GB1,389,237; the $CF_3SO_3H$/silica catalyst disclosed in U.S. Pat. No. 5,220,095, U.S. Pat. No. 5,731,256, U.S. Pat. No. 5,489,729, U.S. Pat. No. 5,364,976, U.S. Pat. No. 5,288,685 and EP0,714,871; the Pt-$AlCl_3$-KCl/$Al_2O_3$ catalyst disclosed in U.S. Pat. No. 5,391,527 and U.S. Pat. No. 5,739,074; the Lewis acid supported catalysts, such as $SbF_5$, $BF_3$ and $AlCl_3$ supported catalysts, disclosed in U.S. Pat. No. 5,157,196, U.S. Pat. No. 5,190,904, U.S. Pat. No. 5,346,676, U.S. Pat. No. 5,221,777, U.S. Pat. No. 5,120,897, U.S. Pat. No. 5,245,101, U.S. Pat. No. 5,012,033, U.S. Pat. No. 5,157,197, CN1,062,307A and WO95/26,815; the supported heteropoly acid catalysts disclosed in CN1,184,797A, CN1,232,814A, U.S. Pat. No. 5,324,881 and U.S. Pat. No. 5,475,178; the molecular sieve catalysts disclosed in U.S. Pat. No. 3,549,557, U.S. Pat. No. 3,644,565, U.S. Pat. No. 3,647,916, U.S. Pat. No. 3,917,738 and U.S. Pat. No. 4,384,161.

WO94/03415 discloses a process for alkylation of an alkane with an olefin, comprising contacting an olefin-containing feed with an isoalkane-containing feed in the presence of crystalline microporous materials, under alkylating conditions including temperatures at least equal to the critical temperature of the principal components and pressures at least equal to the critical pressure of the principal component of the feed. The crystalline microporous materials include various zeolites and layered materials, wherein the zeolites include ZSM zeolites, offretitite zeolite, MCM zeolites, mordenite, REY zeolite etc., and the layered materials include layered silicates and clays etc. When a MCM zeolite is used as the catalyst, said process has an increased butene conversion and an improved catalyst activity stability. However, the olefin conversion in said process is still low, which is only 86.0 to 99.4% by weight.

CN1,125,639A discloses a process for alkylation of isobutane with an olefin, comprising preparing a catalyst by dissolving 10 to 70% of heteropoly acids including $PW_{12}$, $PMo_{12}$, $SiW_{12}$, $PW_{12}Mo_{12-n}$ (n=1-11) etc. in a solvent selected from low-carbon fatty acids, esters, ketones, ethers, alcohols or mixtures of fatty acids and fatty alcohols, to catalyze the alkylation of isobutane with butene, wherein the reaction is carried out at a temperature of 10 to 70° C., and the alkane/olefin ratio is 1.5 to 18. Although said process prevents the equipment from being severely eroded by $H_2SO_4$ and HF catalyst, the problem of isolation of the reaction product from the solvent appears, for the reaction is carried out in a liquid phase. Moreover, said process for alkylation of isobutane with butene has a relatively low olefin conversion and a relatively low alkylate oil yield. For example, according to Examples 1-9, the alkylate oil yield was only 0.693 to 1.736 (relative to the weight of the olefin) in the alkylation performed in a batch reactor.

CN1,125,640A discloses a process for alkylation of isobutane with butene, wherein the alkali salt or ammonium salt of a heteropoly acid selected from phospho-tungstic acid, phospho-molybdic acid, silico-tungstic acid and silico-molybdic acid is used as the catalyst, the varying range (g/molecule) of the alkali metal and the ammonium ion is 0.5 to 3.0 for the phosphor series and 0.5 to 4.0 for the silicon series, the alkylation temperature is 30° C., and the alkane/olefin ratio is 15:1. Said process for alkylation of isobutane with butene still has a relatively low alkylate oil yield, and fails to retain catalyst activity stability. For example, according to the Examples, the alkylate oil yield was at most 1.845, relatively to the weight of the olefin, in the alkylation of isobutane with butene performed in a batch reactor, and the catalytic activity decreased rapidly as the reaction times increased. For example, according to Example 1, $Cs_{2.5}H_{0.5}PW_{12}$ was used as the catalyst, 0.4378 g olefin and an alkane with an alkane/olefin ratio of 15 were added in the reactor, the reaction lasted for 2 hours at 30° C. to produce 0.8118 g alkylate oil, the alkylate oil yield was 1.854, the catalyst was isolated, and used again under the same conditions after dried for 2 hours at 100° C., and the alkylate oil yield was 1.384.

U.S. Pat. No. 5,324,881 discloses a process for alkylation of an isoalkane with an olefin, comprising reacting an isoalkane with an olefin in the presence of a supported heteropoly acid catalyst, under alkylating conditions, thus to obtain an alkylate. The heteropoly acid comprises, as the central element/elements, at least one element selected from the group consisting of P, Si, B, Ge, As, Se, Ti, Zr, Mn, F, V, Ce and Th, and, as the coordinating element/elements, at least one element selected from the group consisting of Mo, W, V, Mn, Co, Ni, Cu, Zn and Fe. According to the examples, all the heteropoly acid catalysts were treated at a temperature above 350° C., the olefin conversion was at most 87% by weight, and the $C_5^+$ alkylate oil yield was at most 1.4 g/g $C_4^+$. The tests prove that said process does not have a satisfactory catalyst activity stability. CN1,232,814A discloses a process for alkylation of a low-carbon isoalkane with an olefin, in which a supported heteropoly acid catalyst is used, the reaction is carried out at a temperature at least equal to the critical temperature of the isoalkane and a pressure at least equal to the critical pressure of the isoalkane. Said process has the advantages of a high olefin conversion and a high alkylate oil yield, as well as improved catalyst activity stability.

CN1,246,467A discloses a process for alkylation of a low-carbon isoalkane with an olefin, characterized in that the catalyst as used consists of 40 to 95% by weight of a porous inorganic support, and 1 to 60% by weight of a Brönsted acid and 0.3 to 15% by weight of a Lewis acid supported on the porous inorganic support, wherein the Brönsted acid is a heteropoly acid or inorganic mineral acid, and the Lewis acid is selected from $AlCl_3$, $BF_3$ or $XF_5$, wherein X is P, As, Sb or Bi. In said process, the active component of the catalyst does not flow away easily, and the conversion and selectivity of the reaction are both relatively high.

CN1,331,065A discloses a process for alkylation of an isoalkane with an olefin over the catalysis of a solid acid, characterized in that the alkylation is carried out by contacting, as the reaction material, a mixture of $C_4$-$C_6$ isoalkane, $C_3$-$C_6$ monoolefin and 10 to 3000 ppm a compound containing a strongly electronegative element as promoter with a solid acid catalyst. The conversion and selectivity of the reaction are both relatively high, and stability of the catalyst is satisfactory.

CONTENTS OF THE INVENTION

One object of the present invention is to provide a process for alkylation of an aromatic hydrocarbon or isoalkane with an olefin over the catalysis of a solid acid, such that the selectivity of the alkylation and in particular the yield of the target product, i.e. dodecyl benzene or trimethyl pentane, can be remarkably increased, and in the meantime stability of the solid acid catalyst is improved.

The inventor of the present invention found out unexpectedly, after conducting a lot of primary researches, that the step of pretreating a solid acid catalyst with a compound having a strongly electronegative element under alkylating conditions not only greatly increases the selectivity of the target product of the alkylation but also improves stability of the solid acid catalyst.

Thus, in the process of the present invention for alkylation of an aromatic hydrocarbon or isoalkane with an olefin, the alkylation is carried out by contacting a reaction material containing an aromatic hydrocarbon or $C_4$-$C_6$ isoalkane, $C_2$-$C_{18}$ monoolefin and a compound containing a strongly electronegative element as promoter with a solid acid catalyst. Said process is characterized in that the solid acid catalyst is contacted with a compound having a strongly electronegative element prior to its contact with the reaction material, wherein said compound having a strongly electronegative element is identical to or different from the compound containing a strongly electronegative element as promoter.

In the alkylation process of the present invention, the step of treating the solid acid catalyst by contacting it with a compound having a strongly electronegative element prior to its contact with the reaction material is the pretreatment of the solid acid catalyst such that it interacts with the compound having a strongly electronegative element. Said compound having a strongly electronegative element is absorbed into the bulk phase of the solid acid catalyst, a new active phase is generated in the solid acid catalyst, and the properties of the acidic center (the density, acid strength and distribution of the acidic center) are changed essentially. In this way, the alkylation begins to proceed in the new active phase at the time of the initial contact of the reaction material with the solid acid catalyst.

In the alkylation process of the present invention, the strongly electronegative element is preferably halogen, and the compound having a strongly electronegative element is comprised preferably in a hydrocarbon, more preferably in an aromatic hydrocarbon or isoalkane. In said aromatic hydrocarbon or isoalkane comprising a compound having a strongly electronegative element, the strongly electronegative element is present in an amount of 10 to 5000 ppm, preferably 30 to 3500 ppm, more preferably 50 to 3000 ppm. The aromatic hydrocarbon is preferably benzene or naphthalene, more preferably benzene. The isoalkane comprising a compound having a strongly electronegative element is one type of $C_4$-$C_6$ isoalkanes, or a mixture of them, preferably one type of $C_4$-$C_6$ isoalkanes, more preferably isobutane.

The compound having a strongly electronegative element may be an inorganic or organic compound, or a mixture of inorganic and organic compounds, wherein the inorganic compound is preferably a hydrogen halide, such as HF, HCl, HBr or HI, more preferably HF or HCl.

The compound having a strongly electronegative element is preferably a halogen-containing organic compound having 2 to 8 carbon atoms, which includes but is not limited to mono- or di-halogenated alkanes each having 2 to 8 carbon atoms, such as monofluorethane, monochlorethane, 1-fluoropropane, 1-chloropropane, 2-fluoropropane, 1-fluorobutane 1-chlorobutane, 1-bromobutane, 2-fluorobutane, 1,3-difluorobutane, 1,3-dichlorobutane, 1-fluoropentane, 1-fluorohexane, 2-fluorohexane, 1-fluoroheptane, 1-fluorooctane, 2-fluorooctane, 1-chlorooctane, fluoro-isooctane and the like, wherein fluoropropane and fluorobutane are preferred.

The inorganic or organic compound containing a strongly electronegative element may be a mixture of two or more of the above compounds. The inorganic or organic compounds that can be decomposed into hydrogen halide or mixtures thereof are suitable for use in the present invention, too.

The aromatic hydrocarbon in the alkylation material is preferably benzene or naphthalene, more preferably benzene; the preferred $C_4$-$C_6$ isoalkane is isobutane, and the $C_2$-$C_{18}$ monoolefin is $C_3$-$C_6$ monoolefin, which is preferably butene.

In the process of the present invention, the aromatic hydrocarbon or isoalkane of a compound having a strongly electronegative element first in contact with the solid acid catalyst can be the same as or different from the aromatic hydrocarbon or isoalkane comprised in the reaction material, and is preferably the same as the aromatic hydrocarbon or isoalkane used in the reaction material. For example, in the alkylation of isobutane with butene, it is preferred to treat the solid acid catalyst with the isobutane of a compound having a strongly electronegative element.

In the process of the present invention, the conditions for the contact of the solid acid catalyst with the aromatic hydrocarbon or isoalkane of a compound having a strongly electronegative element prior to its contact with the reaction material are not particularly restricted. For example, the reaction temperature is 10 to 350° C., the reaction pressure is 0.5 to 10.0 MPa, and the weight hourly space velocity of the aromatic hydrocarbon or isoalkane material is 0.2 to 8 $h^{-1}$. The preferred conditions are supercritical treatment conditions: the treatment temperature ranges from the supercritical temperature of the aromatic hydrocarbon or isoalkane to 300° C., preferably from the supercritical temperature of the aromatic hydrocarbon or isoalkane to 250° C.; the treatment pressure ranges from the supercritical pressure of the aromatic hydrocarbon or isoalkane to 10.0 MPa, preferably from the supercritical pressure of the aromatic hydrocarbon or isoalkane to 80.0 MPa; the weight hourly space velocity of the aromatic hydrocarbon or isoalkane is 0.2 to 20.0 $h^{-1}$, preferably 0.5 to 8.0 $h^{-1}$.

In the process available in the present invention, conditions for the alkylation may be the reaction conditions widely used in the art, and are not particularly restricted. For example, the reaction temperature is 10 to 350° C., the reaction pressure is 0.5 to 10.0 MPa, the mol ratio of the aromatic hydrocarbon or isoalkane to the olefin ranges from 2 to 200, and the weight hourly space velocity of the reaction material is 0.1 to 20 $h^{-1}$. The preferred conditions are supercritical treatment conditions: the reaction temperature ranges from the supercritical temperature of the aromatic hydrocarbon or isoalkane to 300° C., preferably from the supercritical temperature of the aromatic hydrocarbon or isoalkane to 250° C., more preferably from the supercritical temperature of the aromatic hydrocarbon or isoalkane to 200° C.; the reaction pressure ranges from the supercritical pressure of the aromatic hydrocarbon or isoalkane to 10.0 MPa, preferably from the supercritical pressure of the aromatic hydrocarbon or isoalkane to 9.0 MPa, more preferably from the supercritical pressure of the aromatic hydrocarbon or isoalkane to 6.0 MPa; the mol ratio of the aromatic hydrocarbon or isoalkane to the olefin ranges from 2 to 100, preferably from 10 to 90; the weight hourly space velocity (WHSV) of the reaction material ranges from 0.1 to 20 $h^{-1}$, preferably from 0.5 to 8.0 $h^{-1}$.

In the process of the present invention, the solid acid catalyst may be selected from various solid catalysts disclosed in the prior art for alkylation of an aromatic hydrocarbon or isoalkane with an olefin, including supported heteropoly acid catalysts, supported or unsupported heteropoly acid salt catalysts, zeolite-molecular sieve catalysts, $SO_4^{2-}$/oxide super acidic catalysts, supported Brönsted-Lewis conjugate solid super acid catalysts and oxide or molecular sieve catalysts treated with Brönsted acids or Lewis acids. Among these catalysts, the preferred ones are supported heteropoly acid catalysts, supported or unsupported heteropoly acid salt catalysts, supported Brönsted-Lewis conjugate solid super acid catalysts and oxides treated with Brönsted acids or Lewis acids, and more preferred ones are supported heteropoly acid catalysts and supported Brönsted-Lewis conjugate solid super acidic catalysts.

In the process of the present invention, the supported heteropoly acid catalyst consists of a porous inorganic support and a heteropoly acid, wherein the heteropoly acid is represented by the general formula: $H_{8-n}[AM_{12}O_{40}]$, wherein A represents P or Si, M represents W or Mo, and n represents the valence state of A and is 4 or 5; the porous inorganic support is a conventional porous inorganic support selected from activated carbon, silicon oxide, aluminum oxide, magnesium oxide, titanium oxide, natural or synthetic aluminosilicate zeolite, carbon fiber, natural clay and the like, or mixtures thereof, and preferably selected from silicon oxide and aluminum oxide or mixtures thereof. Such catalysts have been described in CN1232814A, which is used here as a reference for the present invention.

In the process of the present invention, the supported or unsupported heteropoly acid salt catalysts are similar to the heteropoly acid catalysts defined above. The difference is that the heteropoly acid salts are the alkali metal salts and ammonium salts of the above-mentioned heteropoly acids.

In the process of the present invention, the supported Brönsted-Lewis conjugate solid super acidic catalyst is as defined in CN1246467A, which is used here as a reference for the present invention. Preferably, it consists of 40 to 95% by weight of a porous inorganic support, and 1 to 60% by weight of a heteropoly acid and 0.3 to 15% by weight of a Lewis acid supported on the porous inorganic support. The heteropoly acid and the porous inorganic support are as defined in the preceding paragraph about the supported heteropoly acid catalyst; the Lewis acid is selected from $AlCl_3$, $BF_3$ or $XF_5$, wherein X represents P, As, Sb or Bi.

In the process of the present invention, the other catalysts are the corresponding conventional catalysts disclosed in the prior art for alkylation of an aromatic hydrocarbon or isoalkane with a olefin. They are not particularly restricted in the present invention.

In the process of the present invention, during the treatment of contacting the solid acid catalyst with the aromatic hydrocarbon or isoalkane comprising a compound having a strongly negative element prior to contact with the reaction material, the form of the reactor is not restricted. The treatment may be carried out in a fixed bed reactor, a batch vessel reactor, or a moving bed, fluidized bed or three-phase slurry bed reactor.

SPECIFIC EMBODIMENTS

The following Examples will further illustrate the present invention, but do not constitute limitations with respect to the contents of the present invention.

The alkylation process of the present invention is carried out in a fixed bed reaction system capable of holding 40 ml catalyst. The reaction system consists of the following three parts:

1. A feed measuring system: The isoalkane material of a compound containing a strongly electronegative element or the reaction material (a mixture of $C_4$-$C_6$ isoalkane, $C_3$-$C_6$ monoolefin and a compound containing a strongly electronegative element as promoter) is pumped from a material tank to a mixer with a precision metering pump (a product of TSP, US), and then to a reactor to be pretreated with a catalyst prior to reaction or to take part in alkylation. The feeding amount is measured by a precision electronic balance under the feed tank, thus ensuring a stable and precise feeding amount.

2. A reaction system: The reactor is capable of holding 40 ml catalyst, and the thermostatic region of a heating furnace ensures uniformity and constancy of the temperature of the catalyst bed. The temperature of the catalyst bed in the reactor is controlled by a temperature controlling device of West, UK. The pressure in the reactor is controlled by a high-precision pressure controlling device (a product of Anaheim, US). Thus, stability and precision of the temperature and pressure in the reactor are ensured.

3. A separating and analyzing system: The reaction product and the unreacted material flowing out of the reactor pass through a high- and low-pressure two stage separator, such that the liquid phase reaction product (alkylate oil) is separated from the gaseous phase unreacted material (isobutene and olefin). The unreacted material is at fixed time analyzed with an on-line gas chromatograph. The alkylate oil is taken out at fixed time and its composition is analyzed with another chromatograph.

Analysis method: The composition of the gaseous product is analyzed on-line with Agilent-4890D gas chromatograph (a product of Agilent Technologies, US), and the chromatographic column is a 50 m×0.2 mm OV-01 capillary crosslink column; the complete composition of the alkylate oil from $C_3$ to $C_{12}$ is analyzed with HP-5890 gas chromatograph (a product of HP, US), and the chromatographic column is a 50 m×0.2 mm OV-01 capillary crosslink column.

Examples 1-3

The solid acid alkylation catalyst used in these Examples is a supported heteropoly acid catalyst. The catalyst is used for alkylation of isobutane with butene.

5.24 g phospho-tungstic acid ($H_3PW_{12}O_{40}\cdot22H_2O$, analytical pure, a product of Beijing Chemical Plant) was measured, and dissolved in 35 ml deionized water to form a $H_3PW_{12}O_{40}$ aqueous solution. 18.5 g silica gel ($SiO_2$, a product of Qingdao Haiyang Chemical Plant) having a particle size of 20 to 40 meshes was put into a filtering flask, in which it was treated at a temperature of 75° C. and a pressure of 0.0095 MPa for 1.0 hour. The temperature was decreased to ambient temperature, and the formulated $H_3PW_{12}O_{40}$ aqueous solution was added under a vacuum condition to infuse the silica gel for 1.0 hour. Then, the mixture was dried at a temperature of 100° C. for 4 hours to produce a supported heteropoly acid catalyst consisting of 20% by weight of $H_3PW_{12}O_{40}$ and 80% by weight of silica gel, which was referred to as 20% $H_3PW_{12}O_{40}/SiO_2$. The resultant catalyst had a specific surface area of 380 $m^2/g$ (measured by low-temperature nitrogen absorption BET method).

10.0 g 20% $H_3PW_{12}O_{40}/SiO_2$ catalyst was measured and put into a 40 ml fixed-bed reactor. Then, nitrogen was introduced, and the temperature and pressure were increased to the temperature and pressure required by solid acid catalyst pretreatment. The isobutane material of a compound containing a strongly electronegative element was pumped at a predetermined flow rate into the reactor by a precision metering pump to contact with the catalyst first (this is referred to as pretreatment hereinafter).

The compositions of the isobutane catalyst pretreatment material and alkylation material used in the Examples are as shown in Table 1.

TABLE 1

| Composition of the isobutane as pretreatment Material, w % | | Composition of the reaction material, w % | |
|---|---|---|---|
| isobutane | 99.99% | propane | 2.81 |
|  |  | n-butane | 2.32 |
|  |  | isobutane | 90.32 |
|  |  | trans-butene-2 | 2.14 |
|  |  | cis-butene-2 | 1.70 |
|  |  | isobutene | 0.52 |
| impurities: |  | impurities: |  |
| $H_2O$ | 4 ppm | $H_2O$ | 18 ppm |
| S | <0.2 mg/$m^3$ | S | <1.0 mg/$m^3$ |
| butadiene | <2 ppm | butadiene | 5 ppm |

Conditions for catalyst pretreatment and alkylation are as shown in Table 2. After the fulfillment of catalyst pretreatment, the alkylation material, a mixture of isobutane, butene and a compound containing a strongly electronegative element as promoter, was pumped at a predetermined flow rate by a precision metering pump, and in the meantime, the nitrogen stream was turned off. After the reaction was stable, the composition of the reaction end gas was analyzed at a fixed time with Agilent-4890D gas chromatograph; the resultant liquid product was taken out at a fixed time and its complete composition was analyzed with HP5890 gas chromatograph.

The alkane/olefin ratio of said reaction material refers to the actual mol ratio of the isoalkane to the monoolefin in the reaction material. 412 ppm HF was added into the isobutane, which was the catalyst pretreatment material, and 252 ppm HF was added into said reaction material as reaction promoter.

Reaction results are listed in Table 2.

Comparative Example 1

This comparative example shows the results produced by using sulfuric acid as the catalyst in alkylation of isobutane with butene.

73.3 g (40 ml) $H_2SO_4$ at a concentration of 95% was used as the catalyst for alkylation of isobutane with butene in a tank reactor. 18.0 g isobutane was added at a reactor pressure (nitrogen pressure) of 7.0 atm. Then, 3.48 g mixed butenes were added when the reaction temperature reached 10° C. with intense agitation. After the reaction lasted for 4.0 hours, the compositions of the gaseous phase and the liquid phase product in the tank were analyzed by gas chromatography. The reaction material is as shown in Table 1. Reaction results are listed in Table 2.

Comparative Example 2

This comparative example illustrates an alkylation process according to the method of CN1331065A. The catalyst, reaction material, alkylation conditions and alkylation steps were identical to those described in Example 1. Reaction results are listed in Table 2.

TABLE 2

|  |  | Example 1 | Example 2 | Example 3 | Comparative Example 1 | Comparative Example 2 |
|---|---|---|---|---|---|---|
| Catalyst pretreatment conditions | Temp., °C. | 60.0 | 140.0 | 240.0 | — | — |
|  | Pressure, MPa | 2.5 | 4.5 | 6.5 | — | — |
|  | WHSV, $h^{-1}$ | 4.0 | 4.0 | 4.0 | — | — |
|  | HF content, ppm | 412 | 412 | 412 | — | — |
|  | Time, hour | 12.0 | 12.0 | 12.0 | — | — |
| Alkylation conditions | Temp., °C. | 140 | 140 | 140 | 10.0 | 140 |
|  | Pressure, MPa | 4.5 | 4.5 | 4.5 | 0.7 | 4.5 |
|  | WHSV, $h^{-1}$ | 3.6 | 3.6 | 3.6 | — | 3.6 |
|  | Alkane/olefin, mole ratio | 20.0 | 20.0 | 20.0 | 20.0 | 22.0 |
|  | HF content, ppm | 252 | 252 | 252 | 0.0 | 252 |
| Sampling time, hour |  | 50 | 1000 | 1200 | 4.0 | 600 |
| $C^=$ olefin conversion, w % |  | 100.0 | 100.0 | 100.0 | 100.0 | 100.0 |
| alkylate yield, g/g |  | 1.99 | 2.01 | 2.00 | 2.01 | 1.99 |
| Reaction product distribution, w % |  |  |  |  |  |  |
| $C_5$ |  | 3.12 | 2.42 | 2.56 | 5.13 | 3.24 |
| $C_6$ |  | 5.01 | 4.43 | 5.46 | 6.05 | 4.56 |
| $C_7$ |  | 5.66 | 6.12 | 6.45 | 5.63 | 6.19 |
| $C_8$ |  | 79.89 | 82.92 | 81.13 | 78.72 | 80.78 |
| $C_9^+$ |  | 6.32 | 4.11 | 4.40 | 4.47 | 5.23 |
| $C_8^=$ |  | 0.00 | 0.00 | 0.00 | 0.00 | 0.00 |
| TMP/DMH |  | 5.97 | 6.36 | 6.11 | 5.61 | 5.42 |
| Octane number of alkylate |  |  |  |  |  |  |
| RON |  | 95.4 | 96.2 | 96.0 | 96.1 | 95.4 |
| MON |  | 93.6 | 94.1 | 94.0 | 94.0 | 93.5 |

In Table 2, TMP represents trimethyl pentanes, DMH represents dimethyl hexanes, RON represents research octane number, MON represents motor-method octane number. RON and MON were obtained according to a document (Huston and Logan, "Estimate Alkyl Yield and Quality", *Hydrocarbon Processing*, September 1975, p 107-108).

It can be seen from Table 2 that upon pretreatment of the catalyst with the isobutane material of a compound having a strongly electronegative element, the catalyst activity ($C_4$ olefin conversion) was retained at 100% and the TMP/DMH mol ratio was kept unchanged (the TMP/DMH mol ratio shows selectivity of the catalyst in the alkylation) after the alkylation lasted for 1200 hours. The $C_8$ isoalkane component in the alkylate oil, i.e. the reaction product of solid acid alkylation obtained according to the process of the present invention, was even higher than that obtained according to the $H_2SO_4$ alkylation process (see Comparative Example 1). In view the results of the alkylation in which the catalyst was not pretreated (see Comparative Example 2), the catalyst had a superior selectivity, more target product, trimethyl pentanes, was produced, and the octane number of the alkylate oil was higher.

Example 4

100 ppm HF was added as the catalyst pretreatment material into the isobutane shown in Table 1, and the catalyst was pretreated under the pretreatment conditions listed in Table 3. The catalyst, alkylation conditions and alkylation steps were identical to those described in Example 1. Reaction results are listed in Table 3.

Example 5

3500 ppm chlorobutane was added as the catalyst pretreatment material into the isobutane shown in Table 1, and the catalyst was pretreated under the pretreatment conditions listed in Table 3. The catalyst, alkylation conditions and alkylation steps were identical to those described in Example 1. Reaction results are listed in Table 3.

TABLE 3

|  |  | Example 4 | Example 5 |
|---|---|---|---|
| Catalyst pretreatment conditions | Temperature, °C. | 140.0 | 140.0 |
|  | Pressure, MPa | 4.2 | 4.2 |
|  | WHSV, $h^{-1}$ | 10.2 | 2.1 |
|  | Content of the compound having a strongly electronegative element, ppm | HF, 100 ppm | Chlorobutane, 3500 ppm |
|  | Treatment time, hour | 26.0 | 6.0 |
| Sampling time, hour |  | 50 | 54 |
| $C^=$ olefin conversion, w % |  | 100.0 | 100.0 |
| alkylate yield, g/g |  | 2.00 | 2.01 |
| Reaction product distribution, w % |  |  |  |
| $C_5$ |  | 2.71 | 2.32 |
| $C_6$ |  | 4.54 | 4.84 |
| $C_7$ |  | 6.37 | 6.78 |
| $C_8$ |  | 82.77 | 82.19 |
| $C_9^+$ |  | 3.61 | 3.87 |
| $C_8^=$ |  | 0.00 | 0.00 |
| TMP/DMH |  | 6.38 | 6.34 |

Examples 6-7

The solid acid alkylation catalyst used in this example was a supported heteropoly acid catalyst.

5.24 g silico-tungstic acid ($H_4SiW_{12}O_{40} \cdot 20H_2O$, analytical pure, a product of Beijing Chemical Plant) was measured, and dissolved in 35 ml deionized water to form a $H_4SiW_{12}O_{40}$ aqueous solution. 18.5 g silica gel ($SiO_2$, a product of Qingdao Haiyang Chemical Plant) having a particle size of 20 to 40 meshes was put into a filtering flask, in which it was treated at a temperature of 75° C. and a pressure of 0.0095 MPa for 1.0 hour. The temperature was decreased to ambient temperature, and the formulated $H_4SiW_{12}O_{40}$ aqueous solution was added under a vacuum condition to infuse the silica gel for 1.0 hour. Then, the mixture was dried at a temperature of 100° C. for 4 hours to produce a supported heteropoly acid catalyst consisting of 20% by weight of $H_4SiW_{12}O_{40}$ and 80% by weight of silica gel, which was referred to as 20% $H_4SiW_{12}O_{40}/SiO_2$. The resultant catalyst had a specific surface area of 376 $m^2/g$.

10.0 g said 20% $H_4SiW_{12}O_{40}/SiO_2$ was used as the catalyst. 250 ppm HCl or 860 ppm 1-flurooctane was added into the isobutane shown in Table 1, and the catalyst was pretreated under the catalyst pretreatment conditions listed in Table 4. Then, alkylation was carried out by using the reaction material shown in Table 1 under the reaction conditions listed in Table 2 according to the reaction steps identical to those described in Example 1. Results are listed in Table 4.

TABLE 4

|  |  | Example 6 | Example 7 |
|---|---|---|---|
| Catalyst pretreatment conditions | Temperature, ° C. | 140.0 | 140.0 |
|  | Pressure, MPa | 4.2 | 4.2 |
|  | WHSV, $h^{-1}$ | 10.2 | 2.1 |
|  | Content of the compound having a strongly electronegative element, ppm | HCl, 250 ppm | 2-fluorooctane, 860 ppm |
|  | Treatment time, hour | 20.0 | 15.0 |
| Sampling time, hour |  | 40 | 42 |
| $C^=$ olefin conversion, w % |  | 100.0 | 100.0 |
| alkylate yield, g/g |  | 1.99 | 2.00 |
| Reaction product distribution, w % |  |  |  |
| $C_5$ |  | 3.71 | 4.32 |
| $C_6$ |  | 4.04 | 4.29 |
| $C_7$ |  | 6.97 | 6.59 |
| $C_8$ |  | 79.01 | 79.01 |
| $C_9^+$ |  | 6.27 | 5.79 |
| $C_8^=$ |  | 0.00 | 0.00 |
| TMP/DMH |  | 5.89 | 6.11 |

Example 8

The solid acid catalyst used in this example was the heteropoly acid salt $Cs_{2.5}H_{0.5}PW_{12}O_{40}$.

22.81 g phospho-tungstic acid, $H_3PW_{12}O_{40} \cdot 21H_2O$ (a product of Beijing Xinhua Chemical Reagent Plant, analytical pure) and 2.85 g $Cs_2CO_3$ (a product of Beitong Chemical Plant, analytical pure) were measured according to the above stoichiometric equations, and formulated to solutions of 0.35 and 0.87 mol concentrations, respectively. With intense agitation, droplets of the $Cs_2CO_3$ solution were added into the $H_3PW_{12}O_{40}$ solution very slowly. Agitation was continued for 30 minutes after the $Cs_2CO_3$ solution was completely added, and then the resultant white precipitate was dried at 50° C. for 24 hours to obtain the heteropoly acid salt $Cs_{2.5}H_{0.5}PW_{12}O_{40} \cdot 8H_2O$. The prepared $Cs_{2.5}H_{0.5}PW_{12}O_{40} \cdot 8H_2O$ was ground, sheeted on a sheeter, crushed into granules, and sieved. The 20-40 mesh granules were taken as the catalyst for use in alkylation.

The catalyst pretreatment conditions and steps were repeated for the pretreatment of the catalyst before alkylation. The alkylation steps described in Example 1 were repeated, except that the catalyst used in Example 1 was replaced by the $Cs_{2.5}H_{0.5}PW_{12}O_{40} \cdot 8H_2O$ catalyst prepared above. Reaction results are listed in Table 5.

Comparative Example 3

The alkylation steps described in Example 8 were repeated, except that the catalyst was not pretreated before reaction. Reaction results were listed in Table 5.

TABLE 5

|  | Example 8 | Comparative Example 3 |
|---|---|---|
| Sampling time, hour | 58 | 56 |
| HF content in the reaction material, ppm | 252 | 252 |
| $C^=$ olefin conversion, w % | 100.0 | 100.0 |
| alkylate yield, g/g | 2.00 | 1.99 |
| Reaction product distribution, w % |  |  |
| $C_5$ | 2.73 | 3.23 |
| $C_6$ | 4.84 | 4.48 |
| $C_7$ | 6.41 | 6.75 |
| $C_8$ | 78.34 | 75.97 |
| $C_9^+$ | 7.68 | 9.57 |
| $C_8^=$ | 0.00 | 0.00 |
| TMP/DMH | 5.94 | 4.99 |

Example 9

The solid acid alkylation catalyst used in this example was a B-L conjugate super acidic acid (B: Brönsted acid, which was $H_3PW_{12}O_{40}$ here; L: Lewis acid, which was $SbF_5$ here).

The catalyst was prepared according to the process described hereinafter. The 20% $H_3PW_{12}O_{40}/SiO_2$ catalyst was first prepared according to the process described in Example 1. Then, 10.0 g said 20% $H_3PW_{12}O_{40}/SiO_2$ catalyst was put into a fixed bed reactor, and treated with a nitrogen stream having a hourly space velocity of 120 $h^{-1}$ at 100° C. for 4 hours. Thereafter, the temperature was decreased to 50° C., and the nitrogen stream was forced to flow through a storage flask containing $SbF_5$, and carried said $SbF_5$ to flow together pass the above-mentioned catalyst, such that $SbF_5$ interacted with the heteropoly acid to produce a B-L acid. Finally, the preparation was fulfilled by purging with the nitrogen stream for 1.0 hour. The resultant catalyst is referred to as $H_3PW_{12}O_{40}$—$SbF_5/SiO_2$ catalyst.

The $H_3PW_{12}O_{40}$—$SbF_5/SiO_2$ catalyst prepared above was employed, and the catalyst pretreatment conditions and steps described in Example 1 were repeated for the pretreatment of the catalyst before alkylation. Then, alkylation was carried out under the alkylation conditions listed in Table 6 according to the reaction steps identical to those described in Example 1. Reaction results are listed in Table 6.

Comparative Example 4

The alkylation steps described in Example 9 were repeated, except that the catalyst was not pretreated before reaction. Reaction results are listed in Table 6.

TABLE 6

|  |  | Example 9 | Comparative Example 4 |
|---|---|---|---|
| Reaction conditions | Reaction temperature, ° C. | 35 | 35 |
|  | Reaction pressure, MPa | 2.2 | 2.2 |

TABLE 6-continued

|  | Example 9 | Comparative Example 4 |
|---|---|---|
| WHSV, h$^{-1}$ | 2.86 | 2.85 |
| Alkane/olefin, mole ratio | 24.2 | 24.2 |
| HF content, ppm | 252 | 252 |
| Sampling time, hour | 42 | 40 |
| C═olefin conversion, w % | 100.0 | 100.0 |
| alkylate yield, g/g | 2.01 | 1.99 |
| Reaction product distribution, w % | | |
| $C_5$ | 3.23 | 3.77 |
| $C_6$ | 3.98 | 4.14 |
| $C_7$ | 5.84 | 5.09 |
| $C_8$ | 83.27 | 83.11 |
| $C_9^+$ | 3.68 | 3.89 |
| $C_8^-$ | 0.00 | 0.00 |
| TMP/DMH | 6.26 | 5.21 |

Example 10

The solid acid alkylation catalyst used in this example was $SO_4^=/ZrO_2$ solid super acid.

20.0 g zirconyl chloride, $ZrOCl_2 \cdot 8H_2O$ (analytic pure, a product of Beijing Chemical Plant) was dissolved in 180 ml water, and droplets of 25% ammonia solution were added into the zirconyl chloride solution slowly at ambient temperature with agitation. Addition of droplets of ammonia and agitation were not stopped until the solution obtained a pH of 10.5. The solution mixture was conditioned at ambient temperature for 24 hours, washed with distilled water, filtered till it was free of Cl$^-$ ions, and dried at 100° C. for 5 hours to produce solid $Zr(OH)_4$. 1.0 M sulfuric acid solution was formulated. Said solid $Zr(OH)_4$ was infused with said 1.0 M sulfuric acid for 4.0 hours at a proportion of 10 ml sulfuric acid solution/1 g $Zr(OH)_4$. Excess acid solution was filtered out. The solid was dried at 100° C. for 3 hours, and then sintered at 550° C. for 4.0 hours to produce $SO_4^=/ZrO_2$ solid super acid. The prepared $SO_4^=/ZrO_2$ solid super acid was ground, sheeted on a sheeter, crushed into granules, and sieved. The 20-40 mesh granules were taken as the catalyst for use in alkylation. The $SO_4^=/ZrO_2$ solid super acidic catalyst prepared above was employed, and the catalyst pretreatment conditions and steps described in Example 1 were repeated for the pretreatment of the catalyst before alkylation. Then, alkylation was carried out under the alkylation conditions listed in Table 7 according to the reaction steps identical to those described in Example 1. Reaction results are listed in Table 7.

Comparative Example 5

The alkylation steps described in Example 10 were repeated, except that the catalyst was not pretreated before reaction. Reaction results are listed in Table 7.

TABLE 7

|  |  | Example 10 | Comparative Example 5 |
|---|---|---|---|
| Reaction conditions | Reaction temperature, ° C. | 155 | 155 |
|  | Reaction pressure, MPa | 4.2 | 4.2 |
|  | WHSV, h$^{-1}$ | 2.16 | 2.16 |
|  | Alkane/olefin, mole ratio | 29.2 | 29.2 |
|  | HF content, ppm | 252 | 252 |
|  | Sampling time, hour | 30 | 30 |
|  | C═olefin conversion, w % | 100.0 | 100.0 |
|  | alkylate yield, g/g | 1.95 | 1.85 |

TABLE 7-continued

|  | Example 10 | Comparative Example 5 |
|---|---|---|
| Reaction product distribution, w % | | |
| $C_5$ | 3.87 | 3.97 |
| $C_6$ | 4.85 | 5.15 |
| $C_7$ | 5.91 | 6.19 |
| $C_8$ | 76.1 | 70.80 |
| $C_9^+$ | 9.27 | 13.89 |
| $C_8^-$ | 0.00 | 0.00 |
| TMP/DMH | 5.02 | 4.11 |

Example 11

The solid acid alkylation catalyst used in this example was an Hβ molecular sieve.

30.0 g Hβ molecular sieve (a product of the Catalyst Plant of Refinery No.3 of Fushun Petrochemical Company) was mixed with ammonium nitride and water at a ratio of 1:0.5:10 to form slurry, which was agitated at 90° C. for 0.5 hour for ion exchange, and then filtered and washed. The ammonium exchange procedure was repeated three times. The filter cake was dried at 110° C. for 3 hours, and then sintered at 550° C. for 6 hours to produce an Hβ molecular sieve. The prepared Hβ molecular sieve was ground, sheeted on a sheeter, crushed into granules, and sieved. The 20-40 mesh granules were taken as the alkylation catalyst.

The Hβ molecular sieve prepared above was employed, and the catalyst pretreatment conditions and steps described in Example 1 were repeated for the pretreatment of the catalyst before alkylation. Then, alkylation was carried out under the alkylation conditions listed in Table 8 according to the reaction steps identical to those described in Example 1. Reaction results are listed in Table 8.

Comparative Example 6

The alkylation steps described in Example 11 were repeated, except that the catalyst was not pretreated before reaction. Reaction results are listed in Table 8.

TABLE 8

|  |  | Example 11 | Comparative Example 6 |
|---|---|---|---|
| Reaction conditions | Reaction temperature, ° C. | 152 | 152 |
|  | Reaction pressure, MPa | 4.5 | 4.5 |
|  | WHSV, h$^{-1}$ | 2.20 | 2.20 |
|  | Alkane/olefin, mole ratio | 28.2 | 28.2 |
|  | HF content, ppm | 252 | 252 |
|  | Sampling time, hour | 25 | 25 |
|  | C═olefin conversion, w % | 100.0 | 100.0 |
|  | alkylate yield, g/g | 1.94 | 1.82 |
| Reaction product distribution, w % | | | |
|  | $C_5$ | 3.35 | 3.89 |
|  | $C_6$ | 4.29 | 5.32 |
|  | $C_7$ | 6.44 | 6.78 |
|  | $C_8$ | 75.22 | 69.69 |
|  | $C_9^+$ | 10.70 | 14.32 |
|  | $C_8^-$ | 0.00 | 0.00 |
|  | TMP/DMH | 4.14 | 3.42 |

Alkylation of benzene with propylene was carried out according to the process of the present invention.

Alkylation of benzene with propylene to produce cumene was carried out in a 250 ml high-pressure reaction tank. 3.0 g supported phospho-tungstic acid (20% $H_3PW_{12}O_{40}/SiO_2$) prepared in Examples 1-3 was added into the reaction tank, and then 60.0 g benzene (analytic pure, a product of Beijing Chemical Plant), which contains 254 ppm HF, was added therein. With intense agitation, the temperature was increased to 75° C., and the mixture was treated at this temperature for 2.5 hours. Then, benzene was discharged out of the reaction tank. Thereafter, 50.0 g benzene containing 110 ppm HF and 7.69 g propylene were added. Alkylation was carried out with intense agitation and stopped after the reaction lasted for 60 minutes. After the temperature dropped to ambient temperature, the amount of the unreacted propylene was measured with a precision flow meter, and the composition of the liquid phase reaction product was analyzed with a chromatograph. Reaction results are listed in Table 9.

Comparative Example 7

The same catalyst and reaction steps as those used in Example 12 were employed, except that the catalyst was not treated with HF-containing benzene before alkylation. Reaction results are listed in Table 9.

TABLE 9

|  | Example 12 | Example 7 |
|---|---|---|
| HF as reaction promoter, ppm | 110 | 110 |
| $C_3^=$ conversion, mol % | 100 | 100 |
| Selectivity of cumene, mol % | 97.2 | 93.1 |

Example 13

Alkylation of benzene with laurylene was carried out according to the process of the present invention.

Alkylation of benzene with laurylene to produce dodecylbenzene was carried out in a 250 ml high-pressure reaction tank. 4.0 g supported phospho-tungstic acid (20% $H_3PW_{12}O_{40}/SiO_2$) prepared in Examples 1-3 was added into the reaction tank, and then 70.0 g benzene (analytic pure, a product of Beijing Chemical Plant), which contains 254 ppm HF, was added therein. With intense agitation, the temperature was increased to 60° C., and the mixture was treated at this temperature for 2.5 hours. Then, benzene was discharged out of the reaction tank. Thereafter, 58.0 g benzene containing 150 ppm HF and 35.7 g laurylene were added. The reaction was carried out with intense agitation and stopped after the reaction lasted for 90 minutes. After the temperature dropped to ambient temperature, the composition of the liquid phase reaction product was analyzed with a chromatograph. Reaction results are listed in Table 10.

Comparative Example 8

The same catalyst and reaction steps as those used in Example 13 were employed, except that the catalyst was not treated with HF-containing benzene before alkylation. Reaction results are listed in Table 10.

TABLE 10

|  | Example 13 | Example 8 |
|---|---|---|
| HF as reaction promoter, ppm | 150 | 150 |
| $C_3^=$ conversion, mol % | 100 | 100 |
| Selectivity of dodecylbenzene, mol % | 98.9 | 94.2 |

The invention claimed is:

1. A process for alkylation of an aromatic hydrocarbon or isoalkane with an olefin using catalysis by a solid acid, comprising contacting a reaction material containing an aromatic hydrocarbon or $C_4$-$C_6$ isoalkane, $C_2$-$C_{18}$ monoolefin and a compound containing a strongly electronegative element, which serves as an promoter, with a solid acid catalyst to carry out the alkylation, characterized in that the solid acid catalyst is contacted with a hydrocarbon comprising a hydrogen halide prior to its contact with the reaction material.

2. The process according to claim 1, wherein said hydrocarbon comprising a hydrogen halide is an aromatic hydrocarbon or isoalkane.

3. The process according to claim 2, wherein said aromatic hydrocarbon or isoalkane comprising a hydrogen halide is the reactant of the alkylation.

4. The process according to claim 2, wherein in said aromatic hydrocarbon or isoallane comprising a hydrogen halide, the hydrogen halide is present in an amount of 10 to 5000 ppm.

5. The process according to claim 4, wherein said hydrogen halide is present in an amount of 30 to 3500 ppm.

6. The process according to claim 5, wherein said hydrogen halide is present in an amount of 50 to 3000 ppm.

7. The process according to any one of claims 3 and 4 to 6, wherein said hydrogen halide is HF or HCl.

8. The process according to claim 2, wherein said isoalkane comprising a hydrogen halide is one of $C_4$-$C_6$ isoalkanes, or a mixture of them.

9. The process according to claim 8, wherein said isoalkane is isobutane.

10. A process for alkylation of an aromatic hydrocarbon or isoalkane with an olefin using catalysis by a solid acid, comprising contacting a reaction material containing an aromatic hydrocarbon or $C_4$-$C_6$ isoalkane, $C_{2\text{-}C18}$ monoolefin and a compound containing a strongly electronegative element, which serves as an promoter, with a solid acid catalyst to carry out the alkylation, characterized in that the solid acid catalyst is contacted with a a hydrogen halide prior to its contact with the reaction material, wherein said solid acid catalyst is a supported heteropoly acid catalyst, a supported or unsupported heteropoly acid salt catalyst, a zeolite molecular sieve catalyst, a $SO_4^{2-}$/oxide super acid catalyst, a supported Brönsted-Lewis conjugate solid super acid catalyst or an oxide or molecular sieve catalyst treated with a Brönsted acid or Lewis acid, and wherein said supported heteropoly acid catalyst consists of a porous inorganic support and a heteropoly acid, wherein the heteropoly acid is represented by the general formula: $H_{8-n}[AM_{12}O_{40}]$, wherein A represents P or Si, M represents W or Mo, and n represents the valence state of A and is 4 or 5; and wherein said supported heteropoly acid salt catalyst consists of a porous inorganic support and a heteropoly acid acid, wherein the heteropoly acid salt is represented by the general formula: $H_{8-n-mx}N_x[AM_{12}O_{40}]$, wherein N is a metal ion selected from alkali metal ions, animonium ion, alkali earth metal ions and metal ions of Group IIIA metals, m represents the valence state of the metal ion, x is a number usable in the range 0<mx<4, A represents P or Si, M represents W or Mo, and n represents the valence state of A and is 4 or 5; said porous inorganic support being a conventional porous inorganic support selected from activated carbon, silicon oxide, aluminum oxide, magnesium oxide, titanium oxide, natural or synthetic aluminosilicate zeolite, carbon fiber and natural clay, or mixtures thereof.

11. A process for alkylation of an aromatic hydrocarbon or isoalkane with an olefin using catalysis by a solid acid, comprising contacting a reaction material containing an aromatic hydrocarbon or $C_4$-$C_6$ isoalkane, $C_2$-$C_{18}$ monoolefin and a compound containing a strongly electronegative element, which serves as an promoter, with a solid acid catalyst to carry out the alkylation, characterized in that the solid acid catalyst is contacted with a hydrogen halide prior to its contact with the reaction material, wherein said solid acid catalyst is a supported heteropoly acid catalyst, a supported or unsupported heteropoly acid salt catalyst, a supported Brönsted-Lewis conjugate solid super acid catalyst or an oxide catalyst treated with a Brönsted acid or Lewis acid, and wherein said supported heteropoly acid catalyst consists of a porous inorganic support and a heteropoly acid, wherein the heteropoly acid is represented by the general formula: $H_{8-n}[AM_{12}O_{40}]$, wherein A represents P or Si, M represents W or Mo, and n represents the valence state of A and is 4 or 5; and wherein said supported heteropoly acid salt catalyst consists of a porous inorganic support and a heteropoly acid acid, wherein the heteropoly acid salt is represented by the general formula: $H_{8-n}[AM_{12}O_{40}]$ wherein N is a metal ion selected from alkali metal ions, ammonium ion, alkali earth metal ions and metal ions of Group IIIA metals, m represents the valence state of the metal ion, x is a number usable in the range $0<mx<4$, A represents P or Si, M represents W or Mo, and n represents the valence state of A and is 4 or 5; said porous inorganic support being a conventional porous inorganic support selected from activated carbon, silicon oxide, aluminum oxide, magnesium oxide, titanium oxide, natural or synthetic aluminosilicate zeolite, carbon fiber and natural clay, or mixtures thereof.

12. The process according to claim 11, wherein said porous inorganic support is silicon oxide, aluminum oxide or a mixture of them.

* * * * *

UNITED STATES PATENT AND TRADEMARK OFFICE
CERTIFICATE OF CORRECTION

PATENT NO. : 7,674,945 B2  Page 1 of 1
APPLICATION NO. : 10/586510
DATED : March 9, 2010
INVENTOR(S) : Yigong He et al.

It is certified that error appears in the above-identified patent and that said Letters Patent is hereby corrected as shown below:

On the Title page Item (73) should read as follows:

Assignee:
China Petroleum & Chemical Corporation, Beijing (CN)
Research Institute of Petroleum Processing, Sinopec, Beijing (CN)

Signed and Sealed this

Twenty-third Day of November, 2010

David J. Kappos
*Director of the United States Patent and Trademark Office*